United States Patent [19]
Kosaka

[11] Patent Number: 5,955,027
[45] Date of Patent: Sep. 21, 1999

[54] REAGENT COMPOSITION, TESTING PIECE, AND ASSAY KIT

[75] Inventor: Hideko Kosaka, Kyoto, Japan

[73] Assignee: Kyoto Daiichi Kagaku Co., Ltd., Kyoto, Japan

[21] Appl. No.: 08/862,676

[22] Filed: May 23, 1997

[30] Foreign Application Priority Data

Jun. 7, 1996 [JP] Japan .................................. 8-146327

[51] Int. Cl.$^6$ ...................................................... G01N 33/48
[52] U.S. Cl. ................................ 422/56; 422/61; 436/169
[58] Field of Search ....................... 422/55–61; 436/164, 436/168, 169, 166

[56] References Cited

U.S. PATENT DOCUMENTS

| | | | |
|---|---|---|---|
| 4,038,077 | 7/1977 | Land | 96/33 |
| 5,439,827 | 8/1995 | Yagi et al. | |
| 5,565,363 | 10/1996 | Iwata et al. | 437/74 |

OTHER PUBLICATIONS

Chemical Abstracts, vol. 81, No. 14, Oct. 7, 1974, Abstract 85601s.
Japanese Abstract—JP59–187266, vol. 9, No. 48 (Kainosu K. K.) Oct. 24, 1984.
Japanese Abstract—JP 4–130056 A, Vo. 18, No. 420 (Tokuyama), May 13, 1994.

*Primary Examiner*—Lyle A. Alexander
*Attorney, Agent, or Firm*—Jones & Askew, LLP

[57] ABSTRACT

A reagent composition for detecting an analyte in a liquid sample, comprising an iron (III) complex of a tetrakis (N-hydroxyalkyl) ethylenediamine represented by the general formula (1):

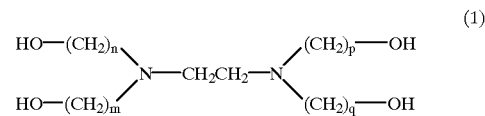

(1)

wherein n, m, p, and q are each independently integers of 1 to 3.

9 Claims, 3 Drawing Sheets

REAGENT COMPOSITION, TESTING PIECE, AND ASSAY KIT

BACKGROUND OF THE INVENTION

1. Field of the Invention

The present invention relates to a reagent composition and a testing piece for measuring a specific component in a liquid sample, and more particularly to a reagent composition, a testing piece, and an assay kit for measuring a specific component, whereby the influence of a reducing substance such as ascorbic acid is eliminated in a liquid sample such as serum, plasma, urine, or culture medium.

2. Description of the Related Art

Various substances having reducing action are contained in liquid samples such as serum, plasma, urine, or culture medium. Examples of such reducing substances include ascorbic acid and uric acid.

During measurement using a testing piece that detects, for example, glucose or occult blood based on a redox reaction, the greater the concentration of reducing substances such as ascorbic acid in the liquid sample, the greater their influence in lowering the measured value of the analyte.

Many methods are thus far known for avoiding the influence of such reducing substances.

For example, Japanese Patent Application Laid-Open No. 52-150692, discloses a method in which such effects are avoided by using ascorbic acid oxidase. A problem in this method, however, is that the ascorbic acid oxidase is expensive and unstable.

Japanese Patent Application Laid-Open No. 59-230161 discloses a method in which copper ions are used to oxidize ascorbic acid. A problem in this method, however, is that the metal ions directly oxidize the redox dye and cause it to color.

Japanese Patent Application Laid-Open No. 56-151358 discloses a method for oxidizing ascorbic acid using an iodate. A problem in this method, however, is that the oxidation properties are too strong, and that the iodine directly oxidizes the redox dye, causing it to color.

In Japanese Patent Application Laid-Open No. 59-187266 (Japanese Patent Publication No. 1-41223), an iron (II) or iron (III) complex of a compound represented by the formula $R_1R_2NCH_2COOH$ or $R_3R_4NXNR_5CH_2COOH$ or an iron (II) or iron (III) complex of gluconic acid is added to eliminate the ascorbic acid during the measurement of components in body fluids. A problem in this method, however, is that the metal ions directly oxidize the redox dye, causing it to color.

In Japanese Patent Application Laid-Open No. 59-193354 (Japanese Patent Publication No. 4-18630), an iron (III) complex of a polycarboxylalkylamine derivative is added to a composition for detecting peroxide active materials. A drawback in this method, however, is that the metal ions directly oxidize the redox dye, causing it to color.

To remedy the aforementioned drawbacks, it has been developed a composition for detecting a peroxide active material (Japanese Patent Application Laid-Open No. 6-148168, U.S. Pat. No. 5,439,827), comprising an organic hydroperoxide, a chromogen, and an iron complex represented by the general formula: $[(OOC—X—COO)_3Fe]Me_3$ wherein X is an alkylene group and M is a monovalent cation. The use of this composition allows the effects caused by reducing substances to be effectively eliminated, but the effects are temperature-dependent. When, for example, measurements are undertaken as the temperature is adjusted to around 37° C. in a device, the measurements can be accurate, but there is still room for improvement during visual measurements while viewing a calorimetric chart at room temperature. There is also room for improving the storage stability of the composition itself.

SUMMARY OF THE INVENTION

The present invention is intended to remedy the aforementioned drawbacks and is intended to provide a reagent composition as well as a testing piece and assay kit, in which storage stability is improved and in which the influence of reducing substances, particularly ascorbic acid, is minimized even at room temperature.

As a result of extensive research to remedy the aforementioned drawbacks, the inventors have found that the storage stability can be improved and that an analyte can be measured in a liquid sample with virtually no effects by ascorbic acid or the like at room temperature when the reagent composition contains an iron (III) complex of a tetrakis (N-hydroxyalkyl)ethylenediamine. Based on this findings, the present invention has been completed.

The present invention provide a reagent composition for detecting an analyte in a liquid sample, comprising an iron (III) complex of a tetrakis(N-hydroxyalkyl)ethylenediamine represented by the general formula (1):

$$HO—(CH_2)_n\underset{HO—(CH_2)_m}{\diagdown}N—CH_2CH_2—N\underset{(CH_2)_q—OH}{\diagup(CH_2)_p—OH} \quad (1)$$

wherein n, m, p, and q are each independently integers of 1 to 3.

Reactive materials or catalysts in redox reactions are examples of analytes. The symbols n, m, p, and q in the general formula (1) for the complex preferably satisfy n=m and p=q.

The present invention also provides a testing piece for detecting an analyte in a liquid sample, which comprises a support and the aforementioned reagent composition supported on the support.

The present invention additionally provides an assay kit for detecting an analyte in a liquid sample, which comprises a reactive material or catalyst for a redox reaction, a chromogen which changes color as a result of the redox reaction, and a complex-containing composition comprising an iron (III) complex of a tetrakis(N-hydroxyalkyl)ethylenediamine represented by the general formula (1).

The present invention makes it possible to provide a reagent composition, a testing piece, and an assay kit, whereby the effects of reducing substances such as ascorbic acid are minimized, even at room temperature, and excellent storage stability is achieved.

DETAILED DESCRIPTION OF THE INVENTION

Figure 1A:
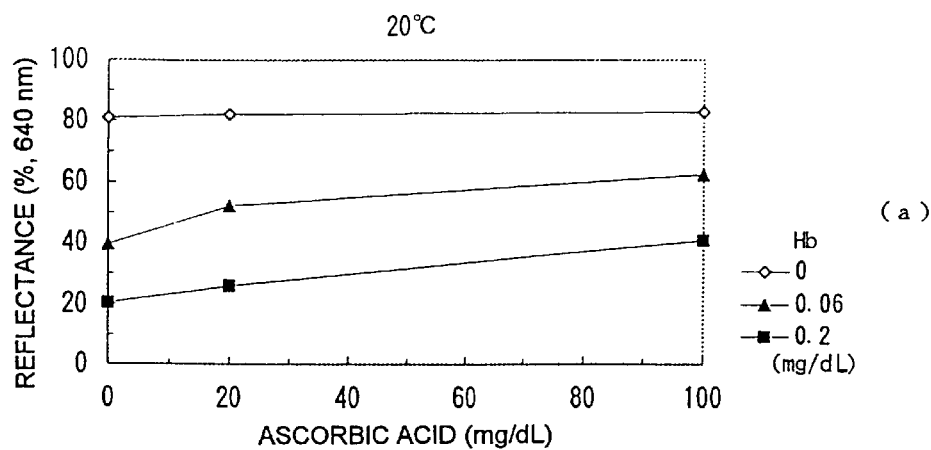
FIG. 1(a–c) depicts the temperature dependency of the testing piece according to the present invention.

The reagent composition according to the present invention is a reagent composition for detecting an analyte in a liquid sample, characterized by comprising an iron (III) complex of a tetrakis(N-hydroxyalkyl)ethylenediamine represented by the general formula (1).

The liquid samples referred to in the present invention include body fluids such as serum, plasma, and urine, and various types of culture medium. Examples of analytes of the reagent composition according to the present invention include components in the aforementioned liquid samples, which can serve as reactive materials or catalysts in redox reactions. Examples of components for detecting analytes in the reagent composition according to the present invention include those which can similarly serve as reactive materials or catalysts in redox reactions. The components for detecting the analyte may be selected as desired depending on the analyte. For example, when occult blood is to be detected, the analyte may be hemoglobin, and the reagent composition may contain a peroxide material and a chromogen which changes color as a result of oxidation. The term "catalyst" used herein includes chemical catalysts and enzymes. The reactive materials mean materials which are converted to another material as a result of a redox reaction, or which undergo a change in oxidation state.

The present invention can be applied to any material which can be detected by a redox reaction. For example, examples of analytes include peroxide materials, glucose, cholesterol, glycerol, pyruvic acid, uric acid, and the like. Components for detecting the analytes contained in the reagent composition should be selected depending on the analyte. For example, if the analyte is glucose, the reagent composition may contain glucose oxidase and be used with a chromogen which changes color with hydrogen peroxide which occurs due to the oxidation of the glucose. Similarly, the reagent composition may contain cholesterol oxidase when the analyte is cholesterol, glycerol oxidase when the analyte is glycerol, pyruvic acid oxidase when the analyte is pyruvic acid, and uric acid oxidase (uricase) when the analyte is uric acid. Examples of chromogens which change color as a result of oxidation include 3,3',5,5'-tetramethylbenzidine, 3,3'-diaminobenzidine, and o-tolidine. The chromogen referred to in the present invention is one which colorizes or discolors, that is, undergoes a change in color, as a result of a chemical reaction, and includes those which emit light, such as fluorescent types.

The reagent composition may contain a chromogen along with the component for detecting the analyte, but for those which can undergo a redox reaction during the storage of the reagent composition, as in the case of peroxide materials and chromogens, the chromogen may be left out of the reagent composition and may be separately prepared in the form of a kit. Kits are described below.

Apart from the fact that the reagent composition according to the present invention contains an iron (III) complex of a tetrakis(N-hydroxyalkyl)ethylenediamine, as described above, it is no different from common reagent compositions for detecting analytes by utilizing a redox reaction.

The reason why the addition of the aforementioned complex provides the effects of the present invention is assumed as follows. When, for example, occult blood is to be detected, hemoglobin is the analyte, and the reagent composition contains a peroxide material and a chromogen which changes color as a result of oxidation. When the reagent composition is dissolved in a sample solution containing hemoglobin, the chromogen oxidizes and changes color as a result of a reaction between the peroxide material and the chromogen due to the peroxidase-like activity of the hemoglobin. A problem with conventional reagents at this time is that when a reducing substance is present in the sample, the measured value is lowered because the oxidation of the chromogen is interfered with the reducing substance. In contrast, the aforementioned complex in the reagent composition according to the present invention can oxidize such reducing substances without oxidizing the chromogen, allowing the analyte to be measured without the influence of these reducing substances. In this way, the reagent composition according to the present invention is particularly effective when the analyte is a reactive material or catalyst in a redox reaction.

In the general formula (1) for the complex used in the present invention, $n=m$ and $p=q$ is preferable, $n=m=p=q$ is more preferable, and $n=m=p=q=2$ is particularly preferable (ethylenediaminetetraethanol).

The reagent composition according to the present invention may be in the form of a powder, granules, tablets or the like, or in the form of a solution.

The reagent composition used in the present invention preferably contains a buffer. The buffer is selected so as to result in a pH at which, depending on the ligands, the complex is stable and shows a suitable oxidation capacity. At this pH, the ligands will not oxidize chromogens such as tetramethylbenzidine, affording a state resulting in a complex which has an oxidizing capacity allowing only reducing substances such as ascorbic acid to be oxidized. The type and amount of the buffer is preferably selected so that the pH of a reagent composition in the form of a liquid, or the pH of an aqueous solution obtained when a reagent composition which is in dry form and which contains the complex is dissolved in water, is preferably within the range of 5 to 8, and even more preferably 5.5 to 7. Although various types of buffer can be used, those demonstrating pronounced buffer effects within this range are preferred. Specific examples include bases such as tris(hydroxymethyl) aminomethane (Tris) and Hepes, and acids such as citric acid, oxalic acid, phosphoric acid, malic acid, and malonic acid, from among which a suitable base and salt may be selected and combined. Of these, a buffer containing tris (hydroxymethyl)aminomethane and malonic acid is particularly suitable.

The reagent composition may also contain a surfactant. That is because a surfactant can improve the reactivity and the sensitivity between the reagent component and the analyte. Any anionic, cationic, nonionic, and amphoteric surfactant can be used, although anionic types, especially sodium diisooctylsulfosuccinate or sodium laurylsulfate, are preferred. Two or more types of surfactants may be used in combination. The reagent composition may also contain a sensitizer such as 2,6-dimethylquinoline. It may also contain a coenzyme or the like which are needed in the assay system.

The testing piece according to the present invention is a testing piece for detecting an analyte in a liquid sample, comprising a support and a reagent composition such as that described above supported on the support.

The support may be one to which the aforementioned reagent composition can be fixed, and any that are commonly used for testing pieces can be used. Specific examples include filter paper, woven fabrics, nonwoven fabrics, glass filters, membrane filters, ceramics, sinters, and the like.

The testing piece according to the present invention can be manufactured by a common method for manufacturing testing pieces using a support and a reagent composition such as that described above. For example, the support may be impregnated with a solution by immersing the support in a solution in which the reagent composition has been dissolved (impregnation solution), or by coating the support with the aforementioned solution, or the like, and the support may then be dried. When a chromogen and an oxidizing material such as a peroxide material are both present at this time, the chromogen may sometimes be oxidized during the storage of the testing piece, so impregnation solutions separately containing the peroxide material and the chromogen is preferably prepared, and the support is impregnated with these impregnation solutions in two stages. When a binder such as polyvinylpyrrolidone is added to one of these solutions at this time, the volatilization of a peroxide material such as cumene hydroperoxide can be prevented, and contact between the chromogen and the peroxide material in the support can be minimized. Either one of the solutions may contain a sensitizer such as 2,6-dimethylquinoline.

The iron (III) complex of a tetrakis(N-hydroxyalkyl) ethylenediamine may be provided in the impregnation solution by first forming a complex of a tetrakis(N-hydroxyalkyl)ethylenediamine and an iron (III) salt, and by then adding the resulting complex to an impregnation solution, or by dissolving the tetrakis(N-hydroxyalkyl)-ethylenediamine and an iron (III) salt in the impregnation solution to form the complex therein. Examples of iron (III) salts include ferric chloride, ferric sulfate, and ferric phosphate.

The impregnation solution containing the reagent composition according to the present invention, that is, the impregnation solution containing the iron (III) complex of a tetrakis(N-hydroxyalkyl)ethylenediamine represented by the general formula (1), is preferably adjusted to a pH of between 5 and 8, and more preferably 5.5 and 7.

The testing piece according to the present invention may be in the form of a strip, and it may be fixed with double-coated adhesive tape to the end of a holder consisting of a piece made of a resin such as polyethylene terephthalate.

The assay kit according to the present invention is an assay kit for detecting an analyte in a liquid sample, comprising a reactive material or catalyst for a redox reaction, a chromogen which changes color as a result of a redox reaction, and a complex-containing composition comprising an iron (III) complex of a tetrakis(N-hydroxyalkyl) ethylenediamine represented by the general formula (1).

The aforementioned complex is contained in the complex-containing composition contained in the assay kit according to the present invention. The complex may be contained without modification in the complex-containing composition, or components constituting the aforementioned complex when dissolved in water may be contained. Examples of components constituting the aforementioned complex when dissolved in water include mixtures of ethylenediaminetetraethanol and ferric chloride.

The complex-containing composition may also contain a buffer such as Tris-malonic acid, a surfactant such as sodium diisooctylsulfosuccinate and sodium laurylsulfate, and an additive such as 2,6-dimethylquinoline, and the like.

The reactive material or catalyst for a redox reaction is a component for detecting the analyte by causing the chromogen to change color as a result of a redox reaction with the chromogen. Specifically, a peroxide material such as cumene hydroperoxide is used in cases where tetramethylbenzidine is used as the chromogen and a substance having peroxide-like activity such as hemoglobin is used as the analyte.

The complex-containing composition may contain a chromogen and a reactive material or catalyst for the redox reaction, but for those which can undergo a redox reaction during the storage of the complex-containing composition, as in the case of peroxide materials and chromogens, the chromogen may be left out of the reagent composition and may be separately prepared in the form of a kit. From the standpoint of decreasing the structural components of the kit, the complex-containing composition preferably contains one of the chromogen and the reactive material or catalyst for the redox reaction.

The complex-containing composition, chromogen, and reactive material or catalyst for the redox reaction may each be in the form of powders, granules, tablets, or the like, or in the form of liquids.

The assay may be carried out by dissolving the complex-containing composition, chromogen, and reactive material or catalyst for the redox reaction in a sample solution, and by measuring the extent of coloring.

EXAMPLE

The present invention is described in detail below with reference to examples, but the present invention is not limited to these examples.

Example 1

Manufacture of Reagent Composition and Testing Piece for Detecting Occult Blood in Urine Various components were mixed according to the following Formulation 1 to prepare a first stage impregnation solution in which the reagent composition according to the present invention was dissolved and a second stage impregnation solution containing a chromogen.

Filter paper (by Whatman, 3MMchr) was impregnated with the first stage impregnation solution, taken out of the liquid, and then air dried for 10 minutes at 50° C. This was then impregnated with the second stage impregnation solution, taken out of the liquid, and then air dried for 10 minutes at 50° C. to obtain a testing piece.

The resulting testing piece was cut to a size of 5 mm×5 mm and then fixed with double-coated adhesive tape to the tip of a 5 mm×80 mm white polyethylene terephthalate (PET) piece which was 0.25 mm thick.

| Formulation 1 | |
|---|---|
| First Stage Impregnation Solution | |
| distilled water | 10 mL |
| 2 M Tris-malonic acid buffer (pH 5.5) | 36 mL |
| ethylenediaminetetraethanol | 1.18 g |
| ferric chloride | 1.35 g |
| cumene hydroperoxide | 4 mL |
| sodium diisooctylsulfosuccinate | 0.3 g |
| sodium laurylsulfate | 0.3 g |
| methanol | 50 mL |
| (first stage impregnation pH: 6.8) | |
| Second Stage Impregnation Solution | |
| 3,3',5,5'-tetramethylbenzidine | 2 g |
| sodium diisooctylsulfosuccinate | 0.3 g |
| 2,6-dimethylquinoline | 1.57 g |
| toluene | 70 mL |

| Formulation 1 | |
|---|---|
| 20% polyvinylpyrrolidone K-30 (by BASF) ethanol solution | 20 mL |

Example 2

Assay Kit for Detecting Occult Blood in Urine

The first and second stage impregnation solutions of Formulation 1 were used as a complex-containing composition solution and a chromogen solution, respectively, to obtain an assay kit for detecting occult blood in urine.

Comparative Example 1

First and second stage impregnation solutions were prepared by mixing various components according to Formulation 2 below, filter paper was impregnated with these impregnation solutions and dried to prepare testing pieces, and the testing pieces were fixed to PET pieces, by the same method as in Example 1.

| Formulation 2 | |
|---|---|
| First Stage Impregnation Solution | |
| distilled water | 10 mL |
| 2 N Tris-malonic acid buffer (pH 5.5) | 36 mL |
| ammonium ferric oxalate | 2.14 g |
| cumene hydroperoxide | 4 mL |
| sodium diisooctylsulfosuccinate | 0.3 g |
| sodium laurylsulfate | 0.3 g |
| methanol | 50 mL |
| Second Stage Impregnation Solution | |
| 3,3',5,5'-tetramethylbenzidine | 2 g |
| sodium diisooctylsulfosuccinate | 0.3 g |
| 2,6-dimethylquinoline | 1.57 g |
| toluene | 70 mL |
| 20% polyvinylpyrrolidone K-30 (by BASF) ethanol solution | 20 mL |

Example 3

Assay of Hemoglobin

Hemoglobin (bovine blood) and ascorbic acid were added in predetermined amounts to human urine and dissolved therein to prepare test urine solutions. The filter components of test pieces of Example 1 and Comparative Example 1 were immersed in the test urine solutions, immediately taken out, and allowed to react for a fixed time at a fixed temperature, and the reflectance at 640 nm was then determined with a color difference meter (model SZ-Σ90, by Nihon Denshoku Kogyo).

The details of measurement are given below.

(1) Temperature Dependence of Influence of Ascorbic Acid

Reactions were brought about by holding, for constant times at 20, 30, and 37° C., test pieces immersed in test urine solutions which had been obtained by adding ascorbic acid in amounts ranging from 0 to 100 mg/dL and hemoglobin in amounts of 0, 0.06, and 0.2 mg/dL, and the influence of ascorbic acid at the various temperatures was then checked by determining the reflectance values. The results for the testing piece of Example 1 are given in FIG. 1, while those for the testing piece of Comparative Example 1 are given in FIG. 2.

Figure 1B:
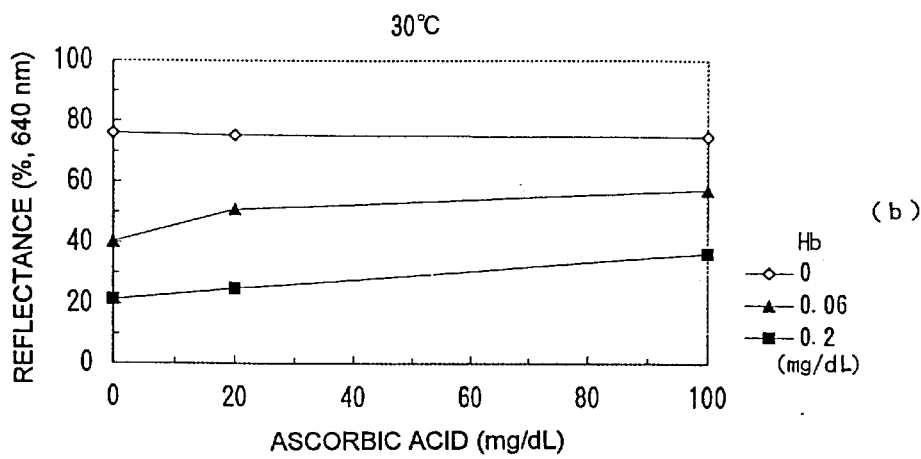
Figure 1C:
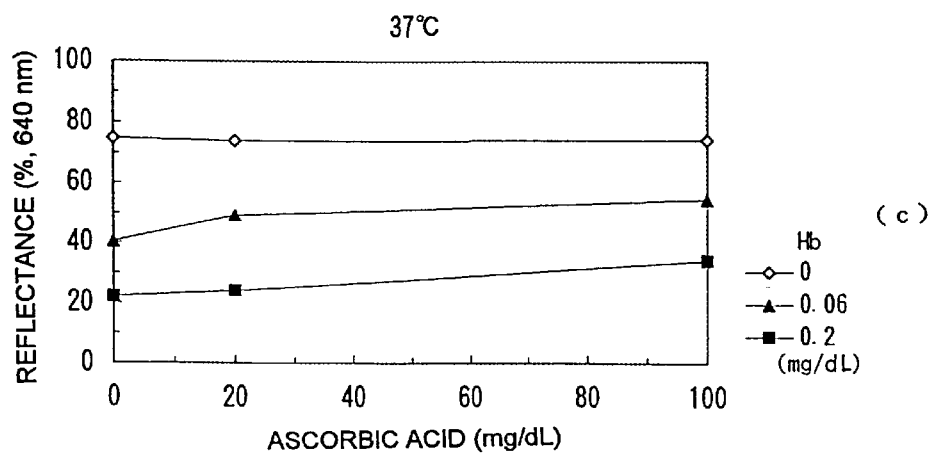
Figure 2A:
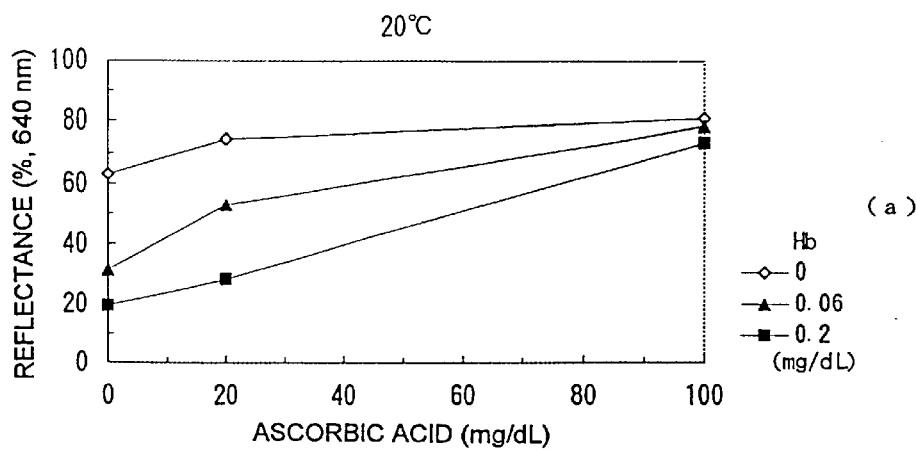
FIG. 2(a–c) depicts the temperature dependency of a testing piece of a comparative example.
Figure 2B:
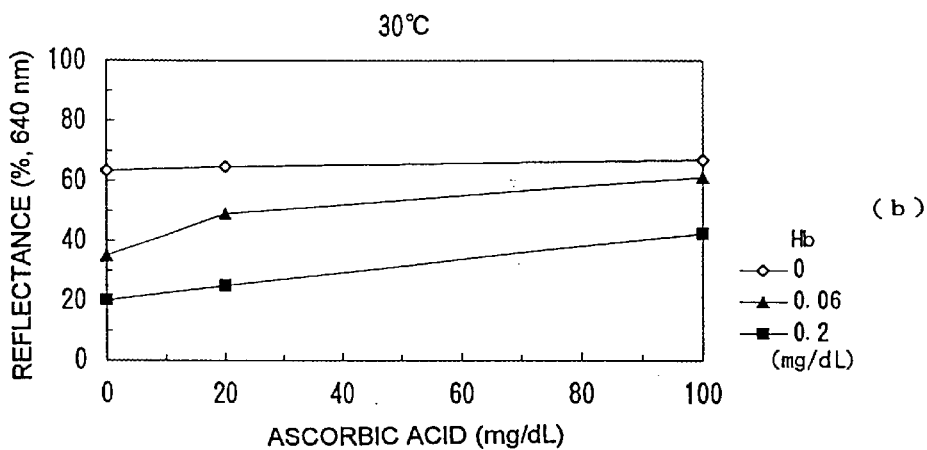
Figure 2C:
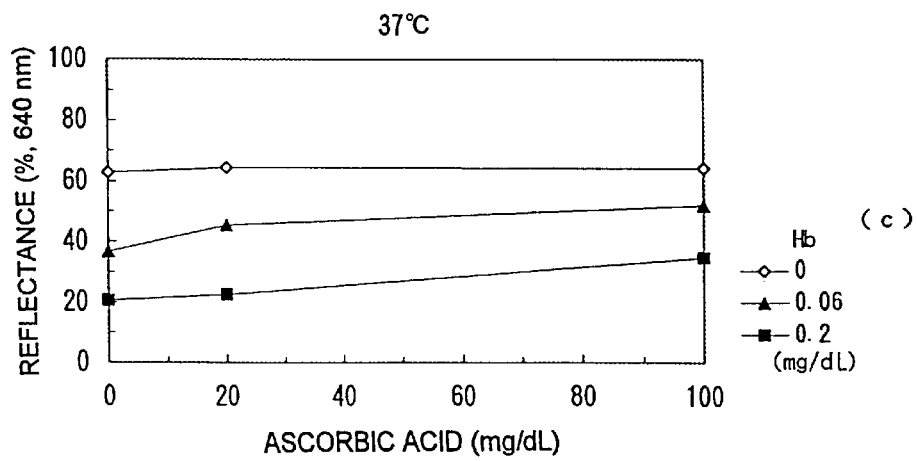

In FIGS. 1 and 2, (a) indicates the results for a temperature of 20° C. during the reaction, (b) indicates the results for 30° C., and (c) indicates the results for 37° C. Hb indicates hemoglobin, and the numerical value underneath indicates the concentration (mg/dL) in samples.

As indicated in the figures, the testing pieces of Example 1 and Comparative Example 1 both turned a favorable blue color when immersed in test urine solutions containing no ascorbic acid and either 0.06 or 0.2 mg/dL hemoglobin.

However, when ascorbic acid was added to the test urine solutions, the testing piece of Comparative Example 1 did not turn the color blue indicating the presence of either 0.06 or 0.2 mg/dL hemoglobin under conditions of a test urine solution temperature of 20° C. and an ascorbic acid concentration of 100 mg/dL.

The testing piece of Example 1, on the other hand, did turn the color blue indicating the presence of 0.2 mg/dL hemoglobin at the various temperatures even in the presence of ascorbic acid at a concentration of 100 mg/dL.

(2) Storage Stability of Testing Pieces

The testing pieces of Example 1 and Comparative Example 1 which were stored at 40° C., were immersed in test urine solutions after a certain period of time had elapsed, and were immediately taken out, and the reflectance was measured. The changes over time in the measured values were monitored to check the storage stability of the testing pieces. The test urine solutions used were prepared with 0, 0.08, and 0.2 mg/dL hemoglobin added and with 0, 20, and 50 mg/dL ascorbic acid added. The measured results for the testing pieces of Example 1 are given in FIG. 3, while those for the testing pieces of Comparative Example 1 are given in FIG. 4.

Figure 3:
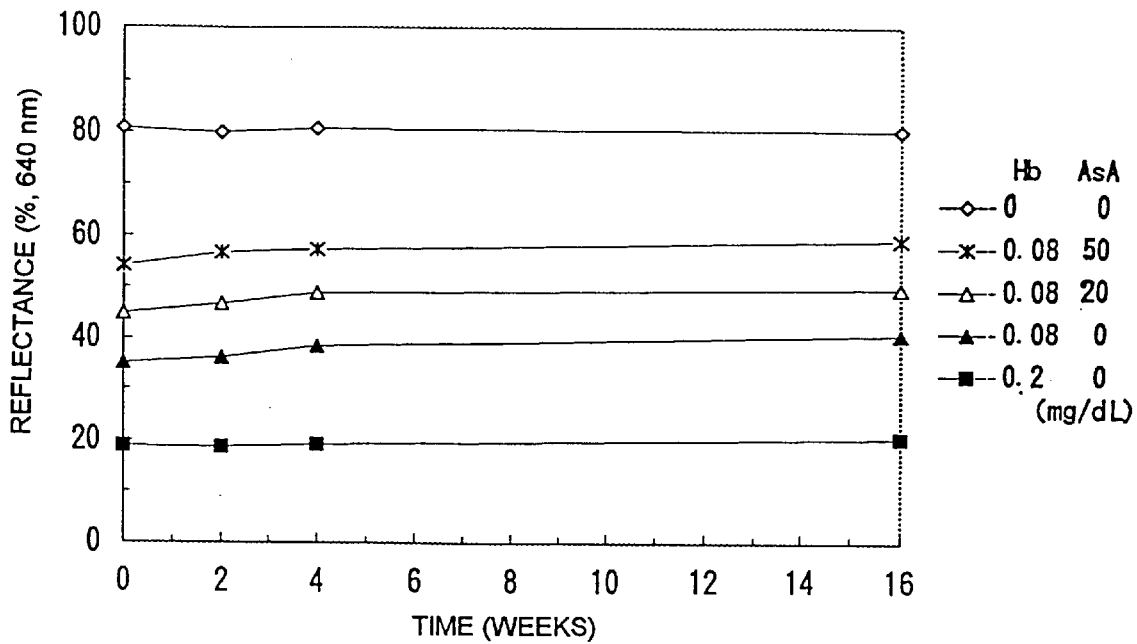
FIG. 3 depicts the storage stability of the testing piece according to the present invention.
Figure 4:
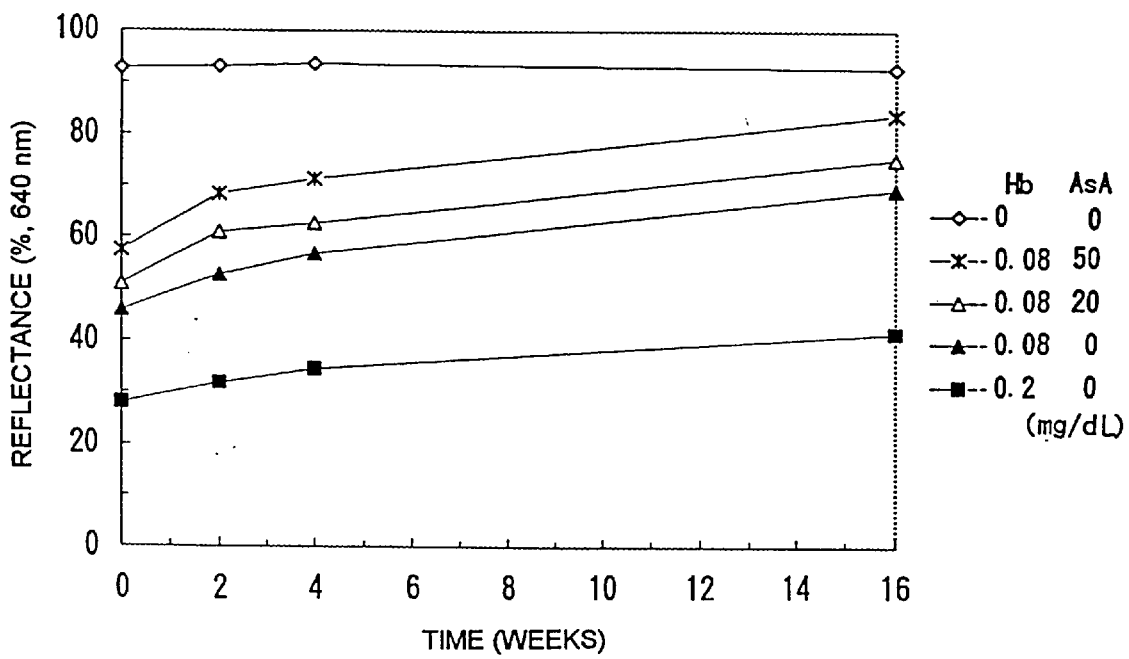
FIG. 4 depicts the storage stability of the testing piece of the comparative example.

In FIGS. 3 and 4, Hb indicates hemoglobin, and AsA indicates ascorbic acid. The numerical values underneath indicate the concentration (mg/dL) in the various samples.

The testing pieces of Example 1 continued to turn a favorable blue color when immersed in the test urine solutions even after 16 weeks of storage at 40° C., whereas the testing pieces of Comparative Example 1 turned less and less blue over time.

In view of the foregoing, it is clear that, compared to the testing pieces of the comparative example, the testing pieces of the present invention were less affected by ascorbic acid at room temperature and were colored more favorably even when stored for a certain period of time. That is, the temperature dependency of the ascorbic acid effects and the storage stability were better.

What is claimed is:

1. A reagent composition for detecting an analyte in a liquid sample, comprising an iron (III) complex of a tetrakis (N-hydroxyalkyl)ethylenediamine represented by the general formula (1):

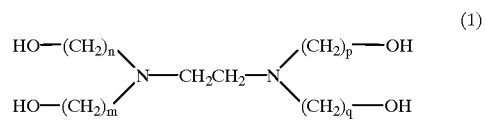

(1)

wherein n, m, p, and q are each independently integers of 1 to 3.

2. A reagent composition according to claim 1, wherein said n, m, p, and q in the general formula (1) as defined in claim 1 satisfy n=m and p=q.

3. A testing piece for detecting an analyte in a liquid sample, which comprises a support and the reagent composition as defined in claim 1 which is supported on the support.

4. A reagent composition according to claim 1, further comprising a surfactant.

5. A reagent composition according to claim 4, wherein said surfactant is selected from the group consisting of sodium diisooctylsulfosuccinate and sodium laurylsulfate.

6. A reagent composition according to claim 1, further comprising a buffer.

7. A reagent composition according to claim 6, wherein said buffer allows pH of an aqueous solution, which is obtained when the reagent composition comprising the complex is dissolved in water, to be adjusted to within a range of 5 to 8.

8. A reagent composition according to claim 6, wherein said buffer is tris(hydroxymethyl)aminomethane and malonic acid.

9. An assay kit for detecting an analyte in a liquid sample, which comprises a reactive material or catalyst for a redox reaction, a chromogen which changes color as a result of the redox reaction, and a complex-containing composition comprising an iron (III) complex of a tetrakis(N-hydroxyalkyl) ethylenediamine represented by the general formula (1):

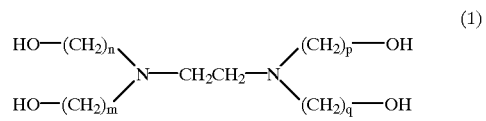

wherein n, m, p, and q are each independently integers of 1 to 3.